US009889440B2

(12) United States Patent
Zhang et al.

(10) Patent No.: US 9,889,440 B2
(45) Date of Patent: Feb. 13, 2018

(54) METHOD FOR SYNTHESIZING SILICOALUMINOPHOSPHATE-34 MOLECULAR SIEVES

(71) Applicant: W. R. GRACE & CO.—CONN., Columbia, MD (US)

(72) Inventors: Qiuhua Zhang, Columbia, MD (US); Manoj M. Koranne, Clarksville, MD (US)

(73) Assignee: W.R. GRACE & CO.—CONN, Columbia, MD (US)

( * ) Notice: Subject to any disclaimer, the term of this patent is extended or adjusted under 35 U.S.C. 154(b) by 105 days.

(21) Appl. No.: 15/031,609

(22) PCT Filed: Oct. 23, 2014

(86) PCT No.: PCT/US2014/061925
§ 371 (c)(1),
(2) Date: Apr. 22, 2016

(87) PCT Pub. No.: WO2015/061544
PCT Pub. Date: Apr. 30, 2015

(65) Prior Publication Data
US 2016/0256860 A1    Sep. 8, 2016

Related U.S. Application Data

(60) Provisional application No. 61/895,087, filed on Oct. 24, 2013.

(51) Int. Cl.
*B01J 29/85* (2006.01)
*C01B 39/54* (2006.01)
*B01J 35/00* (2006.01)
*B01J 35/02* (2006.01)
*B01J 37/04* (2006.01)
*C07C 1/20* (2006.01)

(52) U.S. Cl.
CPC ............. *B01J 29/85* (2013.01); *B01J 35/002* (2013.01); *B01J 35/023* (2013.01); *B01J 37/04* (2013.01); *C01B 39/54* (2013.01); *C07C 1/20* (2013.01); *C07C 2529/85* (2013.01)

(58) Field of Classification Search
CPC ........ B01J 29/85; B01J 35/002; B01J 35/023; B01J 37/04; B01J 37/0018; C01B 39/54; C07C 1/20; C07C 2529/85; C07C 11/107; C07C 31/04; C07C 7/20
See application file for complete search history.

(56) References Cited

U.S. PATENT DOCUMENTS

| | | |
|---|---|---|
| 4,310,440 A | 1/1982 | Wilson et al. |
| 4,440,871 A | 4/1984 | Lok et al. |
| 4,499,327 A | 2/1985 | Kaiser |
| 4,677,243 A | 6/1987 | Kaiser |
| 6,521,562 B1 | 2/2003 | Clem et al. |
| 6,767,858 B1 | 7/2004 | Cao et al. |
| 2003/0153799 A1 | 8/2003 | Mertens et al. |
| 2004/0082466 A1 | 4/2004 | Cao et al. |
| 2005/0075525 A1 | 4/2005 | Chang et al. |
| 2006/0100095 A1 | 5/2006 | Mertens et al. |
| 2006/0100472 A1 | 5/2006 | Mertens et al. |
| 2006/0135349 A1 | 6/2006 | Mertens et al. |
| 2006/0292053 A1 | 12/2006 | Mertens et al. |
| 2007/0249885 A1 | 10/2007 | Chang et al. |
| 2007/0260100 A1 | 11/2007 | Cheng et al. |
| 2007/0276174 A1 | 11/2007 | Martens et al. |
| 2007/0286799 A1 | 12/2007 | Cao et al. |
| 2009/0239737 A1 | 9/2009 | Mertens et al. |
| 2010/0028679 A1 | 2/2010 | Mertens et al. |
| 2010/0087610 A1 | 4/2010 | Vaughn et al. |
| 2012/0202954 A1 | 8/2012 | Mertens et al. |
| 2012/0203046 A1 | 8/2012 | Chae et al. |
| 2013/0108545 A1 | 5/2013 | Miller |

FOREIGN PATENT DOCUMENTS

| | | |
|---|---|---|
| EP | 0 993 867 A1 | 4/2000 |
| WO | 2007/019205 A2 | 2/2007 |

OTHER PUBLICATIONS

International Search Report dated Jan. 22, 2015, issued in counterpart International Application No. PCT/US2014/061925 (2 pages).

*Primary Examiner* — Sharon Pregler
(74) *Attorney, Agent, or Firm* — Westerman, Hattori, Daniels & Adrian, LLP

(57) ABSTRACT

A method for synthesizing small crystals of silicoaluminophosphate-34 (SAPO-34) molecular sieves with high structural purity. The method includes forming a first slurry and a second slurry which are aged separately to form a first aged slurry and a second aged slurry. The first slurry includes a first source of phosphorus, a first source of aluminium, a first source of silicon, and at least one first organic structure directing agent. The second slurry includes a second source of phosphorus, a second source of aluminium, a second source of silicon, and at least one second organic structure directing agent. Then, the first aged slurry and the second aged slurry are combined to form a mixture of aged slurries. Finally, crystallization of silicoaluminophosphate molecular sieves comprising the SAPO-34 molecular sieves is induced from the mixture of aged slurries.

29 Claims, 11 Drawing Sheets

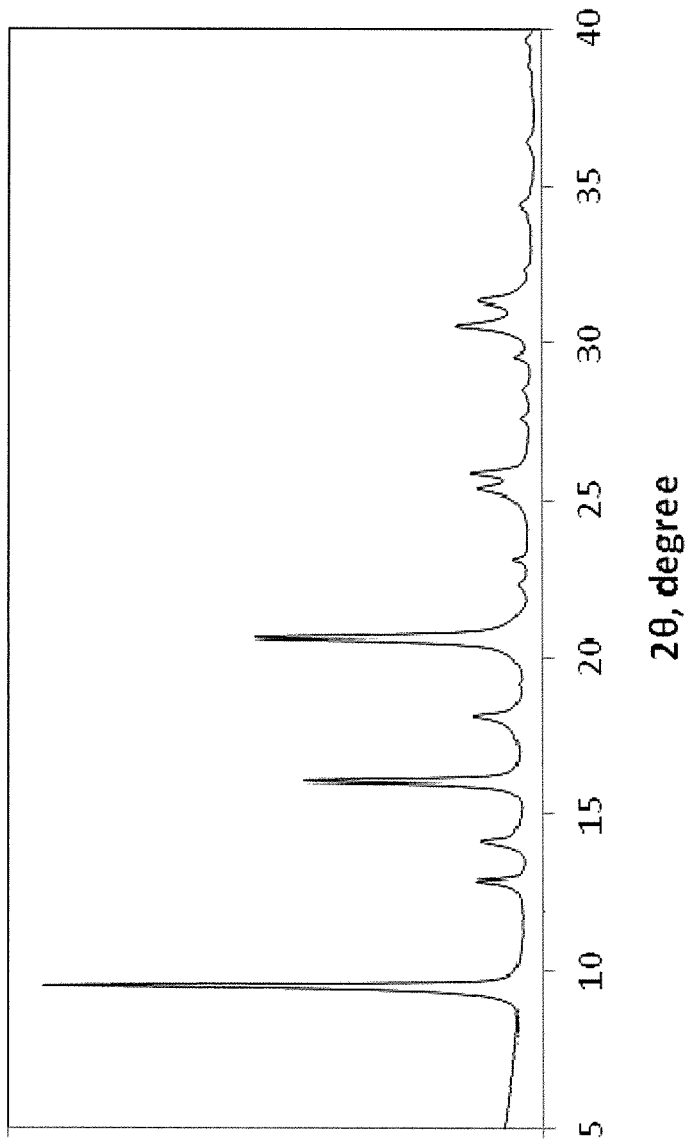

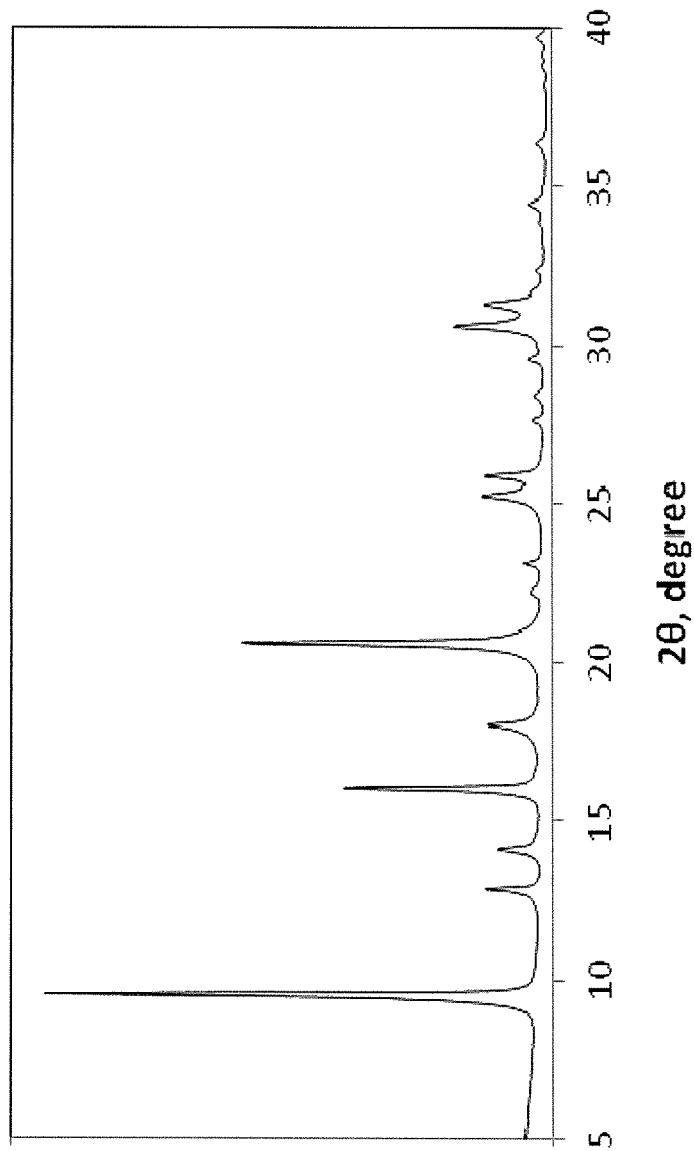

METHOD FOR SYNTHESIZING SILICOALUMINOPHOSPHATE-34 MOLECULAR SIEVES

CROSS-REFERENCE TO RELATED CASES

This application claims the benefit of the filing date of U.S. Provisional Patent Application No. 61/895,087 filed Oct. 24, 2013, the disclosure of which is hereby incorporated by reference.

FIELD OF THE INVENTION

This invention relates to silicoaluminophosphate-34 (SAPO-34) molecular sieves, and more particularly to a method for synthesizing SAPO-34 molecular sieves with high structural purity.

BACKGROUND OF THE INVENTION

Silicoaluminophospate (SAPO) is a material having a three-dimensional microporous crystal framework structure of $PO_2^+$, $AlO_2^-$, and $SiO_2$ tetrahedral units, and whose essential empirical chemical composition in the as-synthesized form and on an anhydrous basis can be represented as follows:

$$mR:(Si_xAl_yP_z)O_2$$

wherein "R" represents at least one organic structure directing agent present in the intracrystalline pore system; "m" represents the moles of "R" present per mole of $(Si_xAl_yP_z)O_2$; and "x," "y," and "z" represent respectively the mole fractions of silicon, aluminium, and phosphorus present in the oxide moiety.

Light olefins are traditionally produced from hydrocarbon feed stocks via thermal cracking of natural gas liquids or petroleum based naphtha and/or fluid catalytic cracking (FCC) of petroleum based feedstocks. With the increasing demand of light olefins, especially ethylene and propylene, alternate routes have been widely explored. Catalytic conversion of alcohols such as methanol to light olefins on molecular sieves is one of the most promising alternative routes to produce ethylene and propylene. This is especially true because methanol may be made from syngas derived from coal, methane, or biomass.

Catalytic conversion of methanol (and other light alcohols) to light olefins using microporous crystallite SAPO molecular sieves has been described by Kaiser (U.S. Pat. No. 4,499,327). The crystal structure, the silicon content and distribution, and the crystal size of the SAPO molecular sieves are among important features of the SAPO molecular sieves for maximizing the selectivity of catalytic conversion to light olefins.

There are a number of different structures of SAPOs which are represented by different framework types. These SAPOs include SAPO-5, SAPO-11, SAPO-18, SAPO-34, SAPO-35, SAPO-41, and SAPO-56. Of these structures, SAPOs represented by framework type CHA (as described in Atlas of Zeolite Framework Types, 2007, 6th Edition, page 96) are known to be selective for the methanol-to-olefins (MTO) reaction (Kaiser, U.S. Pat. No. 4,499,327). In particular, SAPO-34, a CHA framework type with a pore opening of about 4 A and cylindrical cages within the structure of about 10×6.7 Å, is highly selective for the MTO reaction. However, the presence of other SAPOs such as SAPO-5 or SAPO-11 with SAPO-34 tends to produce undesired products (Stud. Surf. Sci. Catal., 61, 429 (1991).

Hence, it is very important to produce SAPO-34 molecular sieves with high structural purity for the MTO reaction.

Furthermore, SAPO-34 molecular sieves with low silicon content and uniform distribution are important for maximizing the selectivity to light olefins in the MTO reaction (Microporous and Mesoporous Materials, 29, 117-126 (1999); Microporous and Mesoporous Materials 53, 97-108 (2002)). Small crystals of SAPO-34 molecular sieves are important to reduce undesired coke formation and improve lifetime of the catalyst (Microporous and Mesoporous Materials 29, 191-203 (1999)). Moreover, features such as flammability, boiling point, toxicity, and amount of the structure directing agent as well as filterability and yields of solid SAPOs recovered during the synthesis have important practical implications for commercial production of SAPO-34 molecular sieves.

During the synthesis of SAPOs, structure directing agents, which are also called templates, are typically used to direct the formation of particular types of framework structures. However, the structure directing agents' effect on the final crystalline structure of SAPOs varies. As a result, it is very difficult to produce relatively pure SAPO-34 structure using structure directing agents currently known to make SAPO-34. Lok et al describe the synthesis of SAPO-34 molecular sieves (along with other SAPO structures) with respect to various structure directing agents and synthesis conditions in U.S. Pat. No. 4,440,871. While certain structure directing agents direct or initiate formation of SAPO-34, other crystalline structures such as SAPO-5 are also formed during the synthesis.

Furthermore, those structure directing agents that are currently known to be more specific for making SAPO-34, such as tetraethylammonium hydroxide (TEAOH), diethylamine (DEA), triethylamine (TEA), or morpholine, have other practical implications. For example, Juan Tan et al discloses that TEA may be used to manufacture small crystal sizes of SAPO-34 (Microporous and Mesoporous Materials, 53 97-108, 2002). However, TEA is volatile, toxic, and relatively noxious, and therefore difficult to use in the commercial production of SAPO-34.

U.S. Pat. No. 4,677,243 discloses a method for synthesizing SAPO-34 using tetraethylammonium hydroxide (TEAOH) as a structure directing agent. While the major phase of the recovered crystalline product is SAPO-34, the product contains other structural impurities. Moreover, this method produces very small crystals of SAPO-34 (less than 1 micron), which are difficult to separate. In addition, TEAOH is also an expensive chemical which limits its practical use in the commercial production of SAPO-34.

US 2012/0203046 A1 also discloses a method for synthesizing SAPO-34 using two structure directing agents, TEAOH and DEA. However, no experimental data is disclosed regarding the structural purity of the solid product separated from the slurry comprising crystallized SAPO-34. Moreover, DEA is volatile, toxic, and relatively noxious, and therefore difficult to use in the commercial production of SAPO-34.

Furthermore, alkanolamines (also named aminoalcohols) either alone or in combination with other structure directing agents are disclosed as suitable to synthesize various types of SAPO frameworks. Alkanolamines have high boiling points, high flashpoints and are relatively less toxic. However, the disclosed synthesis methods using alkanolamines as structure directing agents do not produce SAPO-34 or produce SAPO-34 with low structural purity. For example, Chae et al disclose using N,N-diethanolamine to form SAPO-5, an AFI type of structure. Moreover, Chae et al disclose using triethylamine to form a mixture of SAPO-5 and SAPO-34 (Journal of Nanoscience and Nanotechnology, 10, 195-202, 2010). However, there is no mention of relative structural purity of SAPO-34.

U.S. Pat. No. 4,310,440 describes that ALPO-5, an analogue of SAPO-5, is prepared using triethanolamine, N,N-dimethylethanolamine, N,N-diethylethanolamine, N-methyldiethanolamine, and N-methylethanolamine as structure directing agents. However, there is no mention of synthesis of SAPO-34.

U.S. Pat. No. 6,767,858 discloses a method of synthesizing SAPO-34 using N-methylethanolamine as a structure directing agent at a temperature of 170° C. for 20 hours to 14 days with a SAPO-34 yield of 4.2%. The SAPO-34 yield increases to 27.1% when $HPF_6$ is added as the fluorine source for the synthesis.

European patent application No. 0993867 discloses that SAPO-34 may be prepared using diethanolamine at 200° C. for 60 hours. However, no purity, yield, or physical properties are disclosed. It is also noted that this patent application discloses making SAPO-5 from the same components and the same method by just using different amounts of diethanolamine. In addition, there are no details provided on structural purity or yield of SAPO-5.

Therefore, as discussed above, structure directing agents currently known to form SAPO-34 have limited practical use due to the properties such as high toxicity, low boiling points, and low flashpoints (hence high pressures generated during synthesis). Other structure directing agents, such as alkanolamines which have high boiling points and high flashpoints and are relatively less toxic, do not yield SAPO-34 with high structural purity. Additionally, the methods described in literature do not yield small and highly uniform SAPO-34 crystals necessary for practical use.

BRIEF SUMMARY OF THE INVENTION

Accordingly, one example of the present invention is an inventive method for synthesizing uniform, small crystals of silicoaluminophosphate-34 (SAPO-34) molecular sieves with high structural purity. The Applicants have invented a method that reliably produces uniform, small crystals of SAPO-34 with high structural purity without relying on particular structural directing agents, and it has been shown that the method can do so with certain relatively more environmentally benign structure directing agents such as diethanolamine that are not known to make pure SAPO-34.

The inventive method comprises forming a first slurry and a second slurry which are aged separately to form a first aged slurry and a second aged slurry. The first slurry includes a first source of phosphorus, a first source of aluminium, a first source of silicon, and at least one first organic structure directing agent. The second slurry includes a second source of phosphorus, a second source of aluminium, a second source of silicon, and at least one second organic structure directing agent. At least one first organic structure directing agent in the first slurry is different from at least one second organic structure directing agent in the second slurry. Then, the first aged slurry and the second aged slurry are combined to form a mixture of aged slurries. Finally, crystallization of SAPO molecular sieves comprising the SAPO-34 molecular sieves is induced from the mixture of aged slurries. The obtained SAPO molecular sieves may comprise at least 90% of the SAPO-34 molecular sieves in the crystalline phases.

Another example of the present invention is SAPO-34 molecular sieves which have a chemical composition described on an anhydrous basis as $mR:(Si_x.Al_y.P_z)O_2$, wherein m is in the range of 0.02 to 0.2, x in the range of 0.02 to 0.2, y in the range of 0.3 to 0.6, and z in the range of 0.3 to 0.6.

BRIEF DESCRIPTION OF THE DRAWINGS

FIGS. 2A-2I show x-ray diffraction (XRD) patterns of the solid products obtained from Examples 1 to 6 and Comparative Examples 1 to 3 of the present application respectively.

DETAILED DESCRIPTION OF THE INVENTION

Figure 1:
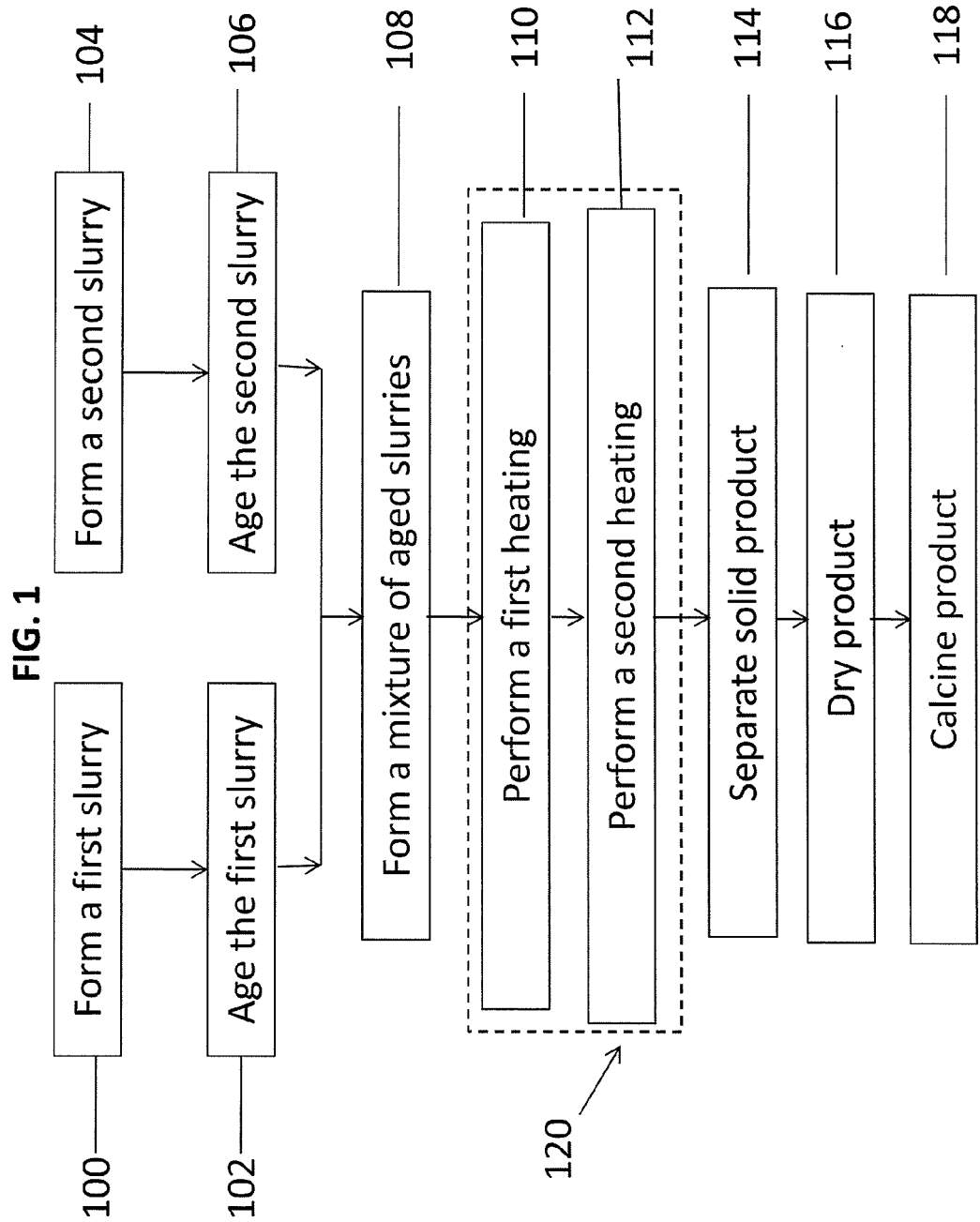
FIG. 1 shows a method for synthesizing silicoaluminophosphate-34 (SAPO-34) molecular sieves in accordance with one embodiment of the present invention.

The present invention is described with reference to embodiments of the invention. Throughout the description of the invention, reference is made to FIGS. 1-3. When referring to the figures, like elements shown throughout are indicated with like reference numerals.

FIG. 1 shows a method for synthesizing silicoaluminophosphate-34 (SAPO-34) molecular sieves in accordance with one embodiment of the present invention. The method includes forming a first slurry and a second slurry which are aged separately to form a first aged slurry and a second aged slurry. The first slurry includes a first source of phosphorus, a first source of aluminium, a first source of silicon, and at least one first organic structure directing agent. The second slurry includes a second source of phosphorus, a second source of aluminium, a second source of silicon, and at least one second organic structure directing agent. At least one first organic structure directing agent in the first slurry is different from at least one second organic structure directing agent in the second slurry. Then, the first aged slurry and the second aged slurry are combined to form a mixture of aged slurries. Finally, crystallization of SAPO molecular sieves comprising the SAPO-34 molecular sieves is induced from the mixture of aged slurries.

Non-limiting examples of suitable first and second sources of phosphorous, which may also include aluminium-containing phosphorus compositions, include phosphoric acid, organic phosphates such as triethyl phosphate, phosphate salts such as ammonium phosphate, tretraethylammonium phosphate, and crystalline or amorphous aluminophosphates such as $AlPO_4$, phosphorus salts, or any combinations thereof. A preferred first or second source of phosphorus is phosphoric acid. Non-limiting examples of suitable first and second sources of aluminium include organoaluminium compounds such as aluminium alkoxides and inorganic aluminium sources such as aluminium phosphate, aluminium hydroxide, sodium aluminate, boehmite, pseudo-boehmite, gibbsite and aluminium trichloride, or any combination thereof. A preferred first or second source of aluminium is pseudo-boehmite.

Non-limiting examples of suitable first and second sources of silicon include alkali silicate such as sodium silicate, fumed silica, organosilicon compounds such as tetraalkyl orthosilicates, for example, tetramethyl orthosilicate (TMOS) and tetraethylorthosilicate (TEOS), colloidal silicas or aqueous suspensions thereof, and silicic acid or any combination thereof. A preferred first or second source of silicon is colloidal silica.

In general, the synthesis of SAPO molecular sieves is a complex interplay between structure directing agents (commonly known as templates), synthesis conditions, and synthesis methodology. It is believed that the structure directing agent or agents direct, or otherwise cause, the silica, alumina, and phosphorus sources to form a structured SAPO framework for forming the desired SAPO structure which, in this case, is SAPO-34.

Illustrative organic structure directing agents are basic nitrogen compounds containing at least one substituted or unsubstituted alkyl group. Preferably, illustrative agents include, but are not limited to, quaternary ammonium compounds, alkanolamines, alkylamines, and combinations thereof. Non-limiting examples of suitable first and second organic structure directing agents include tetraalkyl ammonium compounds and amines including salts and substituted alkyl group connecting to nitrogen thereof, such as tetramethyl ammonium compounds, tetraethyl ammonium compounds, tetrapropyl ammonium compounds, and tetrabutylammonium compounds, cyclohexylamine, morpholine, propylamine, di-n-propylamine (DPA), tripropylamine, diethylamine (DEA), triethylamine (TEA), ethanolamine, N,N-diethanolamine, N,N-diethylethanolamine, isopropanolamine, diisopropanolamine, triisopropanolamine, N,N-dimethylethanolamine, N-methylethanolamine, N-methyldiethanolamine, triethanolamine, methanolamine, dimethanolamine, trimethanolamine, piperidine, cyclohexylamine, 2-methylpyridine, N,N-dimethylbenzylamine, dicyclohexylamine, choline, N,N'-dimethylpiperazine, N',N',N,N-tetramethyl-(1,6)hexanediamine, N-methyl piperidine, 3-methyl-piperidine, N-methylcyclohexylamine, 3-methylpyridine, 4-methyl-pyridine, quinuclidine, di-n-butylamine, neopentylamine, di-n-pentylamine, isopropylamine, diisopropylamine, t-butyl-amine, ethylenediamine, pyrrolidine, and 2-imidazolidone.

As shown in FIG. 1, the synthesizing method includes a forming step 100. At forming step 100, a first slurry is formed. In one embodiment, the amounts of various components added into the first slurry are determined according to the molar ratios shown in the following formula, i.e., $aR.bSiO_2.Al_2O_3.cP_2O_5.dH_2O$ (Formula 1), wherein R is the organic structure directing agent or mixture of two or more different organic structure directing agents, a is the molar ratio of organic structure directing agent or agents to $Al_2O_3$ and varies in the range of 0.1-4.0, b is the molar ratio of $SiO_2$ to $Al_2O_3$ and varies in the range of 0.02-2.0, c is the molar ratio of $P_2O_5$ to $Al_2O_3$ and varies in the range of 0.02-2.0, and d is the molar ratio of $H_2O$ to $Al_2O_3$ and varies in the range of 20 to 100.

At forming step 100, the order of adding the starting components may vary, and the rates of adding the starting components may be 5 g or greater per minute. In one embodiment, the first slurry is formed by first combining a first source of phosphorus and water to form a first phosphoric solution, to which a first source of aluminium is introduced. Then, after the introduction of the first source of aluminium, a first source of silicon is introduced into the first phosphoric solution. Finally, after the introduction of the first source of silicon, at least one first organic structure directing agent is introduced into the first phosphoric solution to form a first slurry. During and after the addition of the starting components, the slurry may be optionally mixed or agitated. The mixing of components may be performed at a temperature ranging from 10° C. to 100° C.

In one embodiment, at least one first organic structure directing agent is a nitrogen compound, preferably selected from the group consisting of quaternary ammonium compounds, alkanolamines, and substituted or unsubstituted alkyl amines, and more preferably selected from compounds known to form SAPO-34 such as tetraethylammonium hydroxide (TEAOH), triethylamine (TEA), diethylamine (DEA), and morpholine. It is even more preferable to use TEAOH. After forming step 100 is completed, the method continues to aging step 102.

At aging step 102, the first slurry is aged. The first slurry may be aged at a temperature ranging from about room temperature to about 200° C., preferably from about 20° C. to about 150° C., for any period of time longer than 0.5 hours, preferably from about 1 hour to about 50 hours, and more preferably from 1 hour to 30 hours. Other methods of aging or assisting in the aging of these slurries include mechanical agitation, and/or milling, and/or sonication.

Without being held to a particular theory, it is believed that at forming step 100, silicon, aluminium, and phosphorus sources disassociate from their respective original forms. At aging step 102, these dissociated species are rearranged to first form SAPO building units, which further form SAPO-34 crystal nuclei precursors in the presence of a structure directing agent or agents that are known to form SAPO-34. These SAPO-34 crystal nuclei precursors may further be converted into SAPO-34 crystal nuclei and/or crystallites under high temperature, hydrothermal conditions at aging step 102. It is preferable that aging step 102 is performed in a manner to maximize the formation of crystal nuclei precursors, nuclei and/or crystallites for SAPO-34 with an optimized combination of parameters such as temperature, time, and concentration in the first aged slurry.

Separately, the synthesizing method also includes a forming step 104. At forming step 104, a second slurry is formed. In one embodiment, the amounts of various components added into the second slurry are determined according to the molar ratios shown in the same formula as that used for the first slurry, as described above, i.e., $aR.bSiO_2.Al_2O_3.cP_2O_5.dH_2O$ (Formula 2), wherein R is the organic structure directing agent or mixture of two or more different organic structure agents of which at least one is different from at least one first organic structure directing agent added in the first slurry, a is the molar ratio of organic structure directing agent or agents to $Al_2O_3$ and varies in the range of 0.1-4.0, b is the molar ratio of $SiO_2$ to $Al_2O_3$ and varies in the range of 0.02-2.0, c is the molar ratio of $P_2O_5$ to $Al_2O_3$ and varies in the range of 0.02-2.0, and d is the molar ratio of $H_2O$ to $Al_2O_3$ and varies in the range of 20 to 100.

At forming step 104, the order of adding the starting components may vary, and the rate of adding various starting components may be 5 g or greater per minute. In one embodiment, the second slurry is formed by first combining a second source of phosphorus and water to form a second phosphoric solution, to which at least one second organic structure directing agent is introduced. Then, after the introduction of at least one second organic structure directing agent, a second source of aluminium is introduced into the second phosphoric solution. Finally, after the introduction of the second source of aluminium, a second source of silicon is introduced into the second phosphoric solution to form a second slurry. Furthermore, at least one second organic structure directing agent in the second slurry is different from at least one first organic structure directing agent in the first slurry. During and after the addition of various starting components, the slurry may be optionally mixed or agitated. The mixing of components may be performed at a temperature ranging from 10° C. to 100° C.

In one embodiment, at least one second organic structure directing agent is a nitrogen compound, preferably selected from the group consisting of quaternary ammonium compounds, alkanolamines, and substituted and unsubstituted alkylamines, and more preferably selected from the group consisting of alkanolamines and alkylamines.

In addition, the second source of phosphorus may be the same or different from the first source of phosphorus. The second source of aluminium may be the same or different from the first source of aluminium. The second source of silicon may be the same or different from the first source of silicon. Therefore, the composition of each slurry (and accordingly, Formulas 1 and 2 above) can be the same in terms of those three components and their molar amounts, and/or the three components and their amounts may be different. As indicated earlier, at least one organic structure directing agent of the second slurry will be different from that in the first slurry, and therefore component R for each formula will be different. The molar ratio "a" for each component R of the two slurries may be the same or different. After forming step 104 is completed, the method continues to aging step 106.

At aging step 106, the second slurry is aged. The temperature used for aging the second slurry preferably should be no higher than 150° C. In one embodiment, the second slurry is aged at a temperature ranging from about 10° C. to about 150° C., preferably from about 20° C. to about 100° C., for a time ranging from about 0.5 hour to about 50 hours, preferably from about 1 hour to about 30 hours. Aging the second slurry at room temperature is particularly suitable if the second slurry may be aged for at least 1 hour, more preferably for 12 hours, and even more preferably for 24 hours.

Without being held to a particular theory, it is believed that at forming step 104, silicon, aluminium, and phosphorus sources in the second slurry disassociate from their respective original forms. At aging step 106, these dissociated species are rearranged into SAPO building units in the presence of a non-particular structure directing agent or agents. The aging conditions at aging step 106 such as temperature and/or time of the aging may be preferably optimized or controlled in a manner to prevent the SAPO building units from further forming crystal nuclei precursors and/or nuclei for SAPO structures other than SAPO-34. Therefore, there are mostly SAPO building units with no or a very small amount of crystal nuclei precursors, nuclei, and/or crystallites for SAPO structures other than SAPO-34 in the second aged slurry. After both aging step 102 and aging step 106 are completed to their desired stage of aging, the method continues to forming a mixture step 108.

At forming a mixture step 108, a mixture of aged slurries is formed by combining the first aged slurry and the second aged slurry under sufficient agitation. The sufficient agitation ensures that the two aged slurries are well mixed and that there are no pockets or areas of inhomogeneity. The weight percentage of the first aged slurry in the mixture of aged slurries may be within the range from about 1% to about 99%, preferably from about 10% to about 80%, and more preferably from about 20% to about 50%. After forming a mixture step 108 is completed, the method continues to inducing crystallization step 120.

At inducing crystallization step 120, crystallization of SAPO molecular sieves comprising the SAPO-34 molecular sieves is induced from the mixture of aged slurries. In one embodiment of the invention, crystallization is induced by a heating protocol using two steps, i.e., a first heating step 110 and a second heating or crystallization step 112.

At first heating step 110, the slurry mixture is additionally aged under a high temperature to ensure the formation and mixing of the crystal nuclei precursors throughout the entire slurry mixture. In one embodiment, the mixture of aged slurries is initially heated to a first temperature ranging from about 50° C. to about 200° C., preferably from about 80° C. to about 150° C., and then held at the first temperature for a time ranging from about 0.5 hour to about 24 hours, preferably from about 1 hour to about 10 hours. It is believed that this further maturation via first heating step 110 induces the formation of a larger population of crystal nuclei which may lead to the formation of uniform, small crystals of SAPO-34 with high structural purity. After first heating step 110 is completed, the method continues to crystallization step 112.

At crystallization step 112, the slurry mixture is further heated to a second temperature and held at the second temperature for a certain amount of time. In one embodiment, the slurry mixture is further heated to a second temperature ranging from about 150° C. to about 250° C., preferably from about 150° C. to about 220° C., and then held at the second temperature for a time ranging from about 0.5 hour to about 70 hours, and preferably from about 1 hour to about 50 hours. In general, this second temperature should be higher than the first temperature at first heating step 110.

Without being held to a particular theory, it is believed that at crystallization step 112, when the first aged slurry comprising crystal nuclei precursors for SAPO-34 is combined with the second aged slurry comprising SAPO building units under a crystallization temperature, the crystal nuclei precursors for SAPO-34 "direct" or enable the SAPO building units to form SAPO-34 molecular sieves with high structural purity. It is believed that the presence of such crystal nuclei precursors for SAPO-34 may be critical for producing SAPO-34 crystals with high structural purity. In addition, the SAPO-34 molecular sieves obtained are small in size and relatively uniform in its size distribution. In one embodiment, the average diameter of SAPO-34 crystals is smaller than 3 μm.

Another embodiment of inducing crystallization step 120 may include a single heating step protocol, in which the mixture of aged slurries is heated to a temperature that is the same as the second temperature at crystallization step 112, but at a heating rate not faster than 10° C. per minute. In one embodiment, the mixture of aged slurries is heated to a temperature within the range from about 150° C. to about 250° C., preferably from about 150° C. to about 220° C., and then holding the mixture at the temperature for a time within the range from about 0.5 hour to about 70 hours, preferably from about 1 hour to 50 hours. After inducing crystallization step 120 is completed, the method continues to separating step 114.

At separating step 114, SAPO molecular sieves comprising the SAPO-34 molecular sieves are recovered from the product slurry. Separating step 114 may include filtration of the SAPO solids from the product slurry and washing of the SAPO solids. Non-limiting examples of filtration equipments include vacuum filtration using filter cloth or paper, filter belts, filter presses, centrifuges, and/or membrane filters. Separating step 114 may be performed at a temperature ranging from 10 to 100° C., and preferably from room temperature to 70° C. In one embodiment, the solid SAPO molecular sieves may be separated by a filtration step through filters such as belt filters, filter presses, and membrane filters, and/or through centrifuges. The separated solid SAPO molecular sieves are then washed by water. The washing may be performed using filtration equipment described above with the temperature of the washing water ranging from 10 to 100° C., and preferably from room temperature to 70° C. The purpose of the washing is to remove the residual compounds/salts from the recovered SAPO solids. The number of washing steps and the amount and pH of washing water are adjusted to ensure that the recovered SAPO solids are devoid of any impurities. For example, if sodium silicate is used as a silicon precursor, it may be advantageous to acidify the washing water to remove the residual sodium impurity from the recovered SAPO solids. After separating step 114, the solid SAPO molecular sieves are collected. The water content in the solid SAPO molecular sieves may be less than 80% by weight, and preferably less than 60% by weight. After separating step 114 is completed, the method continues to drying step 116.

At drying step 116, the SAPO molecular sieves comprising the SAPO-34 molecular sieves are dried to become free flowing powders. In one embodiment, the SAPO molecular sieves comprising the SAPO-34 molecular sieves are dried in a static oven, flash dryer, and/or tumbling dryer at a temperature ranging from 50° C. to 250° C., and preferably from 80° C. to 150° C. under the atmospheric condition or a flow of gas such as air. The water content in the SAPO molecular sieves after drying step 116 may be less than 20%, and preferably less than 10%.

After drying step 116 is completed, the solid products obtained comprise at least 90% of SAPO-34 and preferably 95% of SAPO-34 in the crystalline phase. The SAPO-34 molecular sieves may have a chemical composition described on an anhydrous basis as $mR:(Si_x.Al_y.P_z)O_2$ wherein m is in the range of 0.02 to 0.2, x in the range of 0.02 to 0.2, y in the range of 0.3 to 0.6, and z in the range of 0.3 to 0.6. After drying step 116 is completed, the method continues to calcining step 118.

At calcining step 118, the SAPO molecular sieves comprising the SAPO-34 molecular sieves are calcined to remove or burn off the residual organic structure directing agent or agents. The SAPO molecular sieves comprising the SAPO-34 molecular sieves may be calcined in a static furnace, moving bed furnace and/or rotary calciner at a temperature ranging from 350° C. to 750° C. under the atmospheric condition or a flow of gas such as air, oxygen, or nitrogen. Air is preferred. The calcination conditions are adjusted in a manner such that the total carbon left behind from the residual organic structure directing agent or agents in the calcined solid product may be not more than 5%, and preferably not more than 1%. The total weight loss of the calcined solid product may be not more than 15%, and preferably not more than 10% at 850° C. for 5 hours.

In one embodiment, the recovered SAPO molecular sieves comprise at least 90% of the SAPO-34 molecular sieves. In another embodiment, the recovered SAPO molecular sieves comprise at least 95% of the SAPO-34 molecular sieves.

The SAPO molecular sieves comprising the SAPO-34 molecular sieves from separating step 114, drying step 116 and/or calcining step 118 may be further combined with formulating agents such as a matrix material and a binding agent to form catalyst particles. In one embodiment, the SAPO molecular sieves used to make catalyst particles comprise one or more metal elements from groups 1 to 14 such as transition metal elements. The metal elements may be incorporated by introducing metal containing compounds such as metal salts or/and hydroxides to the slurries during any of the synthesis steps from forming step 100 to forming a mixture step 108. In another embodiment, metal containing compounds may be introduced into SAPO molecular sieves after crystallization step 112 through physical mixing, ion-exchange, and/or impregnation.

The particle size of these catalyst particles may be in a range from 10 microns to 5 millimeters depending on the type of reactor operation. For example, for a fluidized bed reactor, an average particle size from 10-150 microns, preferably from 50-100 microns, is suitable. For a fixed bed operation, an average particle size from 1 mm-5 mm, preferably from 1.5-3 mm, is suitable.

The weight percentage of the SAPO molecular sieves comprising the SAPO-34 molecular sieves on a dry basis in the catalyst particles may be from 20 to 90%. The matrix material is preferably selected from clays such as kaolin, with a weight percentage ranging from 20 to 90% in the catalyst particles. The matrix material may be one or a combination of two or more materials. The matrix material typically plays the role of a filler to reduce cost and/or control diffusion of reactants and products throughout the catalyst particles.

The binding agents may comprise aluminium based or silicon based binders. Non-limiting examples of binding agents include aluminium nitrate, aluminium chloride, aluminium chlorohydrol, aluminium sulphate, aluminium phosphate, peptized alumina, peptized aluminium hydroxide, alumina sol, silica sol, and any combination thereof, with a weight percentage ranging from 5% to 30% in the catalyst particles. The binding agent is used to bind catalytically active component such as SAPO-34 in this invention with the matrix material such as clays to form shaped particles with desirable strength.

The SAPO molecular sieves comprising the SAPO-34 molecular sieves and the formulating agents may be mixed with or without mechanical grinding, and the mixture is then converted into particles of desirable size and shape, followed by a calcination step at a temperature ranging from 200° C. to 700° C. for a time ranging from 1 hour to 10 hours under the atmospheric condition or a flow of gas such as air. In one embodiment, the mixture is spray dried to form spherical particles with an average size ranging from 10 to 200 μm, and preferably from 50 to 100 μm.

The formulated catalyst may be used in the conversion of light oxygenates to light olefins. The light oxygenate feedstocks include alcohols, aldehydes, ketones, ethers, or mixtures thereof, and more preferably light alcohols and ethers containing 1-6 carbon atoms. It is particularly advantageous to use SAPO-34 of high structural purity, as disclosed herein, for the conversion of methanol to olefins (MTO) as described by Kaiser (U.S. Pat. No. 4,499,327).

Hereinafter, the present invention will be described in more detail with reference to Examples. However, the scope of the present invention is not limited to the following Examples.

EXPERIMENTS

Structural purity in this invention is defined as the percentage of SAPO-34 in the total crystalline materials that are resulted from the synthesis routes.

The structural purity of SAPO-34 in the SAPO molecular sieves is calculated based on the diffraction patterns of XRD measurement. A characteristic X-ray diffraction (XRD) pattern of the SAPO-34 molecular sieves of this invention is set forth in Table 1.

TABLE 1

| 2θ, degree | d-spacing, Å | Relative Intensity, % |
|---|---|---|
| 9.57 | 9.24 | 100.0 |
| 12.88 | 6.87 | 8.4 |
| 14.13 | 6.27 | 6.4 |
| 16.04 | 5.53 | 25.8 |
| 18.04 | 4.92 | 6.3 |
| 19.13 | 4.64 | 0.7 |
| 20.60 | 4.31 | 42.7 |
| 22.19 | 4.01 | 1.4 |
| 23.10 | 3.85 | 1.9 |
| 25.27 | 3.52 | 7.6 |
| 25.85 | 3.45 | 7.9 |
| 27.62 | 3.23 | 1.0 |
| 28.40 | 3.14 | 1.1 |
| 28.50 | 3.14 | 1.0 |
| 29.56 | 3.02 | 2.0 |
| 30.56 | 2.92 | 12.9 |
| 31.29 | 2.86 | 9.3 |
| 32.32 | 2.77 | 1.0 |
| 33.88 | 2.64 | 0.5 |
| 34.41 | 2.60 | 1.9 |
| 36.38 | 2.47 | 1.2 |
| 38.10 | 2.36 | 0.2 |
| 38.89 | 2.31 | 0.6 |
| 39.67 | 2.27 | 1.2 |

The structural purity of SAPO-34 (SAPO-34%) is then calculated according to the formula below:

$$SAPO\text{-}34\% = \frac{A_{sapo34}}{A_{sapo34} + A_{sapo5} + A_{other} + A_{unknown}} \times 100\%$$

wherein $A_{sapo34}$ is the area of the XRD peak at 2θ=9.6°±0.2°; $A_{sapo5}$ is the area of the XRD peak at 2θ=7.4°±0.2°; $A_{other}$ is the area of the most intense peak of any other identified phase not associated with SAPO-5 and SAPO-34; and $A_{unknown}$ is the combined area of all unidentified peaks that are not associated with SAPO-5, SAPO-34 and any other identified phases.

The samples for all XRD measurement are prepared by drying 5 gram of solid products obtained from separating step 114 during the synthesis at 120° C. for 5 hours. The dried solid products are further crushed into powders if necessary for XRD measurement.

Crystal size is measured under SEM, where two areas of samples are randomly selected and imaged under various magnifications. The average of diameters of one hundred SAPO-34 crystals, fifty in each selected area, is taken.

Example 1

229.3 g of 85% phosphoric acid ($H_3PO_4$) and 181.1 g of $H_2O$ were first combined under agitation to form a diluted $H_3PO_4$ solution. Then, 132.4 g of Catapal® B alumina (registered trademark of Sasol North America Inc.) was added portion-wise under agitation to the diluted $H_3PO_4$ solution to form a homogeneous mixture. After the addition of Catapal® B alumina was completed, 90.1 g Ludox® AS-40 (40% $SiO_2$) (registered trademark of W.R. Grace & Co.-Conn.) was added into the mixture under agitation until the mixture became homogeneous. Finally, after the addition of Ludox® AS-40 was completed, 841.5 g of 35% tetraethylammonium hydroxide (TEAOH) was added into the mixture under agitation to form a first slurry. The final composition of the first slurry is $2.0TEAOH/0.6SiO_2/1.0Al_2O_3/1.0P_2O_5/50H_2O$. The first slurry was further stirred at room temperature for about 24 hours to obtain a first aged slurry.

Separately, 183.4 g of 85% phosphoric acid ($H_3PO_4$) and 745.6 g of $H_2O$ were combined to form a diluted $H_3PO_4$ solution. Then, 303.6 g of triethylamine (TEA) was added under agitation to the diluted $H_3PO_4$ solution to form a homogeneous mixture. After the addition of TEA was completed, 132.4 g of Catapal® B alumina was added into the mixture under agitation until the mixture became homogeneous. Finally, after the addition of Catapal® B was completed, 90.1 g of Ludox® AS-40 was added into the mixture under agitation to form a second slurry. The final composition of the second slurry is $3.0TEA/0.6SiO_2/1.0Al_2O_3/1.0P_2O_5/50H_2O$. The second slurry was further stirred at room temperature for about 24 hours to obtain a second aged slurry.

A mixture of aged slurries was prepared by combining 200 g of the first aged slurry and 400 g of the second aged slurry under agitation. The mixture of aged slurries was transferred to a 1 L autoclave with an agitation rate of at least 200 rpm. The mixture of aged slurries was heated to a temperature of about 200° C. and held at the temperature for 8 hours under autogenous pressure. The obtained solid products were filtered, washed, dried, and calcined.

Figure 2A:
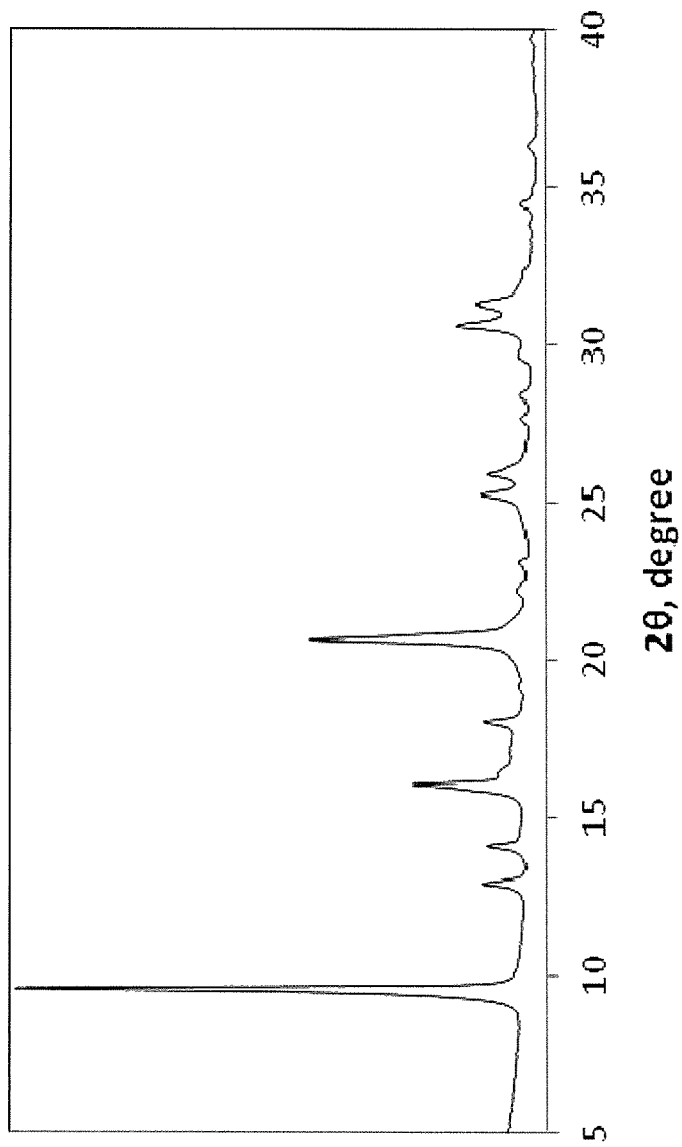

The X-ray diffraction (XRD) pattern of the solid products obtained from Example 1 is shown in FIG. 2A. The structural purity of SAPO-34 is measured to be 100%. In addition, the SAPO-34 molecular sieves obtained are small in size and relatively uniform in its size distribution. The average diameter of SAPO-34 crystals is smaller than 3 μm.

Example 2

A first slurry was prepared in the same way of preparing the first slurry in Example 1. The first slurry was further stirred at room temperature for about 24 hours to obtain a first aged slurry.

Separately, 56.3 g of 85% phosphoric acid ($H_3PO_4$) and 228.8 g of $H_2O$ were combined to form a diluted $H_3PO_4$ solution. Then, 46.6 g of triethylamine (TEA) was added under agitation to the diluted $H_3PO_4$ solution to form a homogeneous mixture. After the addition of TEA was completed, 40.6 g of Catapal® B alumina was added into the mixture under agitation until the mixture became homogeneous. Finally, after the addition of Catapal® B was completed, 27.6 g of Ludox® AS-40 was added into the mixture under agitation to form a second slurry. The final composition of the first slurry is $1.5TEA/0.6SiO_2/1.0Al_2O_3/1.0P_2O_5/50H_2O$. The second slurry was further stirred at room temperature for about 24 hours to obtain a second aged slurry.

A mixture of aged slurries was prepared by combining 200 g of the first aged slurry and 400 g of the second aged slurry under agitation. The mixture of aged slurries was transferred to a 1 L autoclave with an agitation rate of at least 200 rpm. The mixture of aged slurries was initially heated to a temperature of 120° C. and held at the temperature of 120° C. for 5 hours under autogenous pressure. Then, the mixture of aged slurries was further heated to a temperature of 200° C. and held at the temperature of 200° C. for 8 hours under autogenous pressure. The obtained solid products were filtered, washed, dried, and calcined.

Figure 2B:
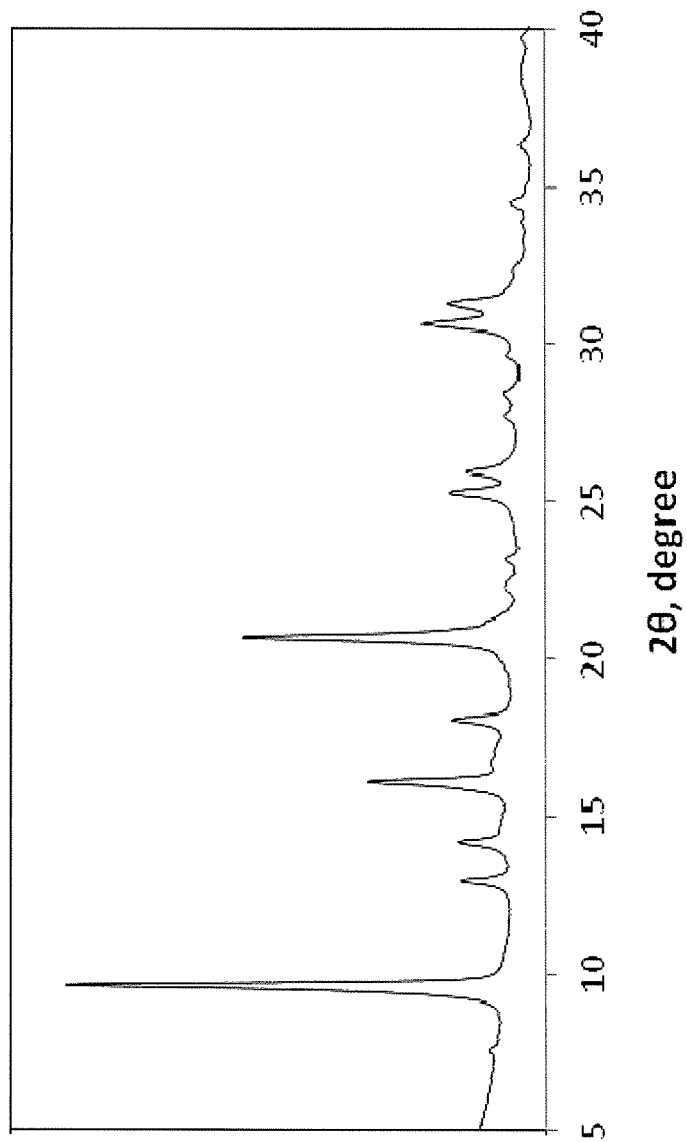

The X-ray diffraction (XRD) pattern of the solid products obtained from Example 2 is shown in FIG. 2B. The structural purity of SAPO-34 is measured to be 99%. In addition, the SAPO-34 molecular sieves obtained are small in size and relatively uniform in its size distribution. The average diameter of SAPO-34 crystals is smaller than 3 μm.

Example 3

A first slurry was prepared in the same way of preparing the first slurry in Example 1. The first slurry was further aged at 80° C. for about 16 hours to obtain a first aged slurry.

Separately, 65.0 g of 85% phosphoric acid ($H_3PO_4$) and 197.9 g of $H_2O$ were combined to form a diluted $H_3PO_4$ solution. Then, 37.5 g of Catapal® B alumina was added under agitation to the diluted $H_3PO_4$ solution to form a homogeneous mixture. After the addition of Catapal® B was completed, 34.14 g of Ludox® AS-30 (30% $SiO_2$) was added into the mixture under agitation until the mixture became homogeneous. Finally, after the addition of Ludox® AS-30 was completed, 65.5 g of diethanolamine (DEtA) was added into the mixture under agitation to form a second slurry. The final composition of the second slurry is $2.2DEtA/0.6SiO_2/1.0Al_2O_3/1.0P_2O_5/50H_2O$. The second slurry was further stirred at room temperature for about 24 hours to obtain a second aged slurry.

A mixture of aged slurries was prepared by combining 200 g of the first aged slurry and 400 g of the second aged slurry under agitation. The mixture of aged slurries was transferred to a 1 L autoclave with an agitation rate of at least 200 rpm. The mixture of aged slurries was initially heated to a temperature of 120° C. and held at the temperature of 120° C. for 5 hours under autogenous pressure. Then, the mixture of aged slurries was further heated to a temperature of 190° C. and held at the temperature of 190° C. for 8 hours under autogenous pressure. The obtained solid products were filtered, washed, dried, and calcined.

Figure 3:
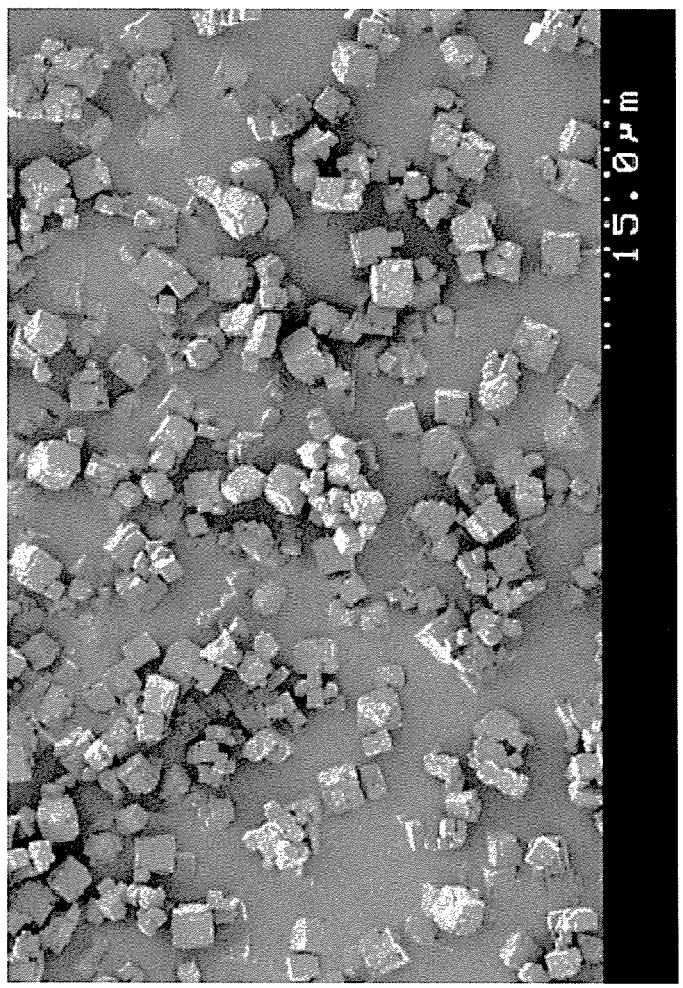
FIG. 3 shows a scanning electron microscope (SEM) image of the solid products obtained from Example 3 of the present application.

The X-ray diffraction (XRD) pattern of the solid products obtained from Example 3 is shown in FIG. 2C. The structural purity of SAPO-34 is measured to be 100%. In addition, FIG. 3 shows a SEM image of the solid products obtained. The SAPO-34 molecular sieves obtained are small in size and relatively uniform in its size distribution. The average diameter of SAPO-34 crystals is smaller than 3 μm.

Example 4

A first aged slurry and a second aged slurry were prepared in the same way of preparing the first aged slurry and the second aged slurry in Example 3 respectively.

A mixture of aged slurries was prepared by combining 200 g of the first aged slurry and 400 g of the second aged slurry under agitation. The mixture of aged slurries was transferred to a 1 L autoclave with an agitation rate of at least 200 rpm. The mixture of aged slurries was initially heated to a temperature of 120° C. and held at the temperature of 120° C. for 5 hours under autogenous pressure. Then, the mixture of aged slurries was further heated to a temperature of 175° C. and held at the temperature of 175° C. for 16 hours under autogenous pressure. The obtained solid products were filtered, washed, dried, and calcined.

The X-ray diffraction (XRD) pattern of the solid products obtained from Example 4 is shown in FIG. 2D. The structural purity of SAPO-34 is measured to be 100%. In addition, the SAPO-34 molecular sieves obtained are small in size and relatively uniform in its size distribution. The average diameter of SAPO-34 crystals is smaller than 3 μm.

Example 5

A first slurry was prepared in the same way of preparing the first slurry in Example 1. The first slurry was further stirred at room temperature for about 24 hours to obtain a first aged slurry.

Separately, 67.5 g of 85% phosphoric acid ($H_3PO_4$) and 205.7 g of $H_2O$ were combined to form a diluted $H_3PO_4$ solution. Then, 39.0 g of Catapal® B alumina was added under agitation to the diluted $H_3PO_4$ solution to form a homogeneous mixture. After the addition of Catapal® B was completed, 35.4 g of Ludox® AS-30 was added into the mixture under agitation until the mixture became homogeneous. Finally, after the addition of Ludox® AS-30 was completed, 52.4 g of monoisopropanolamine (MiPA) was added into the mixture under agitation to form a second slurry. The final composition of the second slurry is $2.2MiPA/0.6SiO_2/1.0Al_2O_3/1.0P_2O_5/50H_2O$. The second slurry was further stirred at room temperature for about 24 hours to obtain a second aged slurry.

A mixture of aged slurries was prepared by combining 200 g of the first aged slurry and 400 g of the second aged slurry under agitation. The mixture of aged slurries was transferred to a 1 L autoclave with an agitation rate of at least 200 rpm. The mixture of aged slurries was initially heated to a temperature of 120° C. and held at the temperature of 120° C. for 5 hours under autogenous pressure. Then, the mixture of aged slurries was further heated to a temperature of 190° C. and held at the temperature of 190° C. for 16 hours under autogenous pressure. The obtained solid products were filtered, washed, dried, and calcined.

Figure 2E:
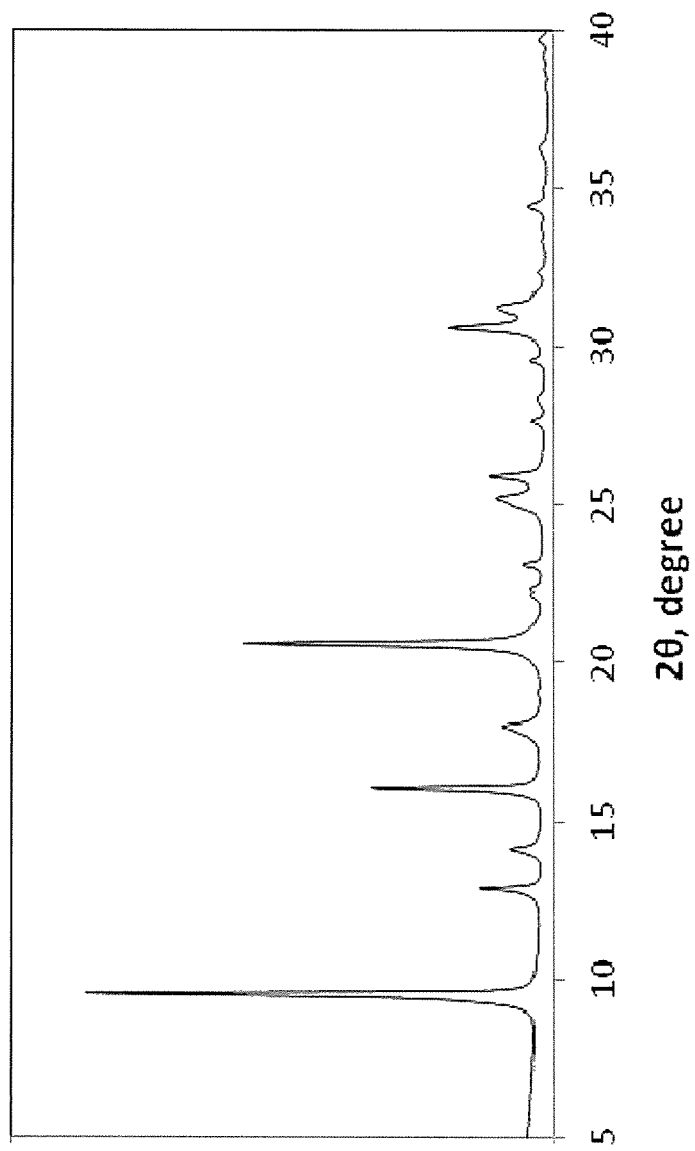

The X-ray diffraction (XRD) pattern of the solid products obtained from Example 5 is shown in FIG. 2E. The structural purity of SAPO-34 is measured to be 100%. In addition, the SAPO-34 molecular sieves obtained are small in size and relatively uniform in its size distribution. The average diameter of SAPO-34 crystals is smaller than 3 μm.

Example 6

A first slurry was prepared in the same way of preparing the first slurry in Example 1. The first slurry was further stirred at room temperature for about 24 hours to obtain a first aged slurry.

Separately, 3.1 g of 85% phosphoric acid ($H_3PO_4$) and 9.5 g of $H_2O$ were combined to form a diluted $H_3PO_4$ solution. Then, 1.8 g of Catapal® B alumina was added under agitation to the diluted $H_3PO_4$ solution to form a homogeneous mixture. After the addition of Catapal® B was completed, 1.6 g of Ludox® AS-30 (30% $SiO_2$) was added into the mixture under agitation until the mixture became homogeneous. Finally, after the addition of Ludox® AS-30 was completed, 4.0 g of diisopropanolamine (DiPA) was added into the mixture under agitation to form a second slurry. The final composition of the second slurry is $2.2DiPA/0.6SiO_2/1.0Al_2O_3/1.0P_2O_5/50H_2O$. The second slurry was further stirred at room temperature for about 24 hours to obtain a second aged slurry.

A mixture of aged slurries was prepared by combining 10 g of the first aged slurry and 20 g of the second aged slurry under agitation. The mixture of aged slurries was transferred to a 50 ml Teflon-lined stainless steel autoclave. The mixture of aged slurries was initially heated to a temperature of 120° C. and held at the temperature of 120° C. for 2 hours under autogenous pressure. Then, the mixture of aged slurries was further heated to a temperature of 190° C. and held at the temperature of 190° C. for 16 hours under autogenous pressure. The obtained solid products were filtered, washed, dried, and calcined.

Figure 2F:
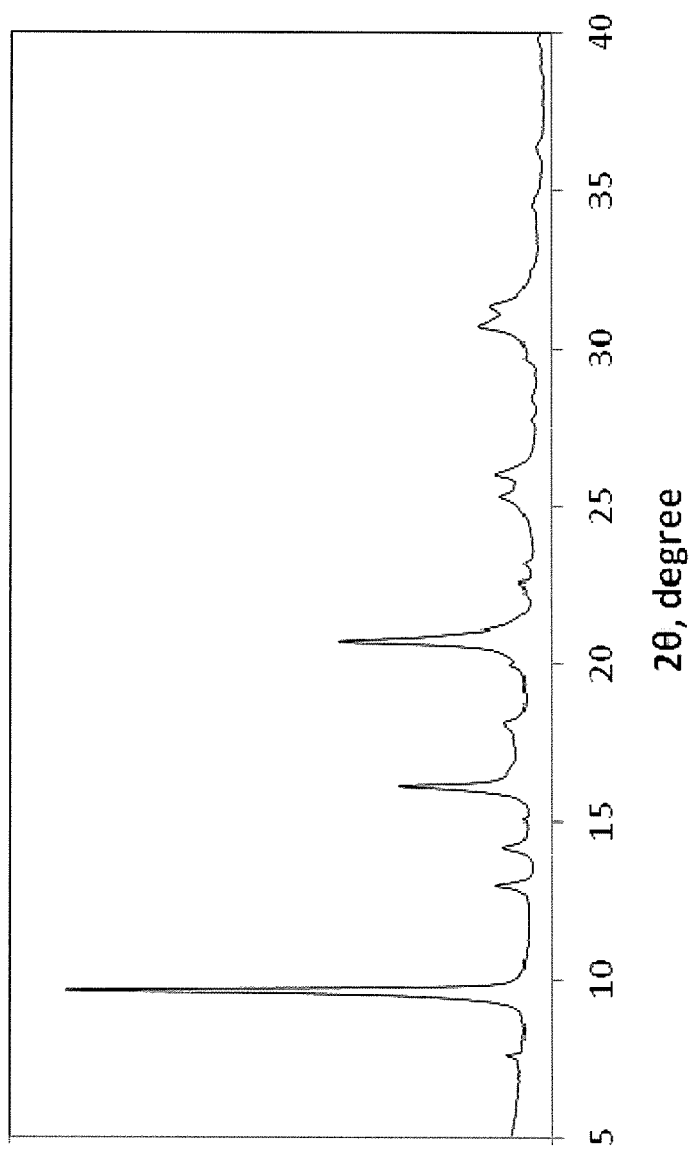

The X-ray diffraction (XRD) pattern of the solid products of Example 5 is shown in FIG. 2F. The structural purity of SAPO-34 is measured to be 98%. In addition, the SAPO-34 molecular sieves obtained are small in size and relatively uniform in its size distribution. The average diameter of SAPO-34 crystals is smaller than 3 μm.

Comparative Example 1

A slurry was prepared in the same way of preparing the second slurry in Example 1. The slurry was then aged and crystallized under the same conditions in Example 1.

Figure 2G:
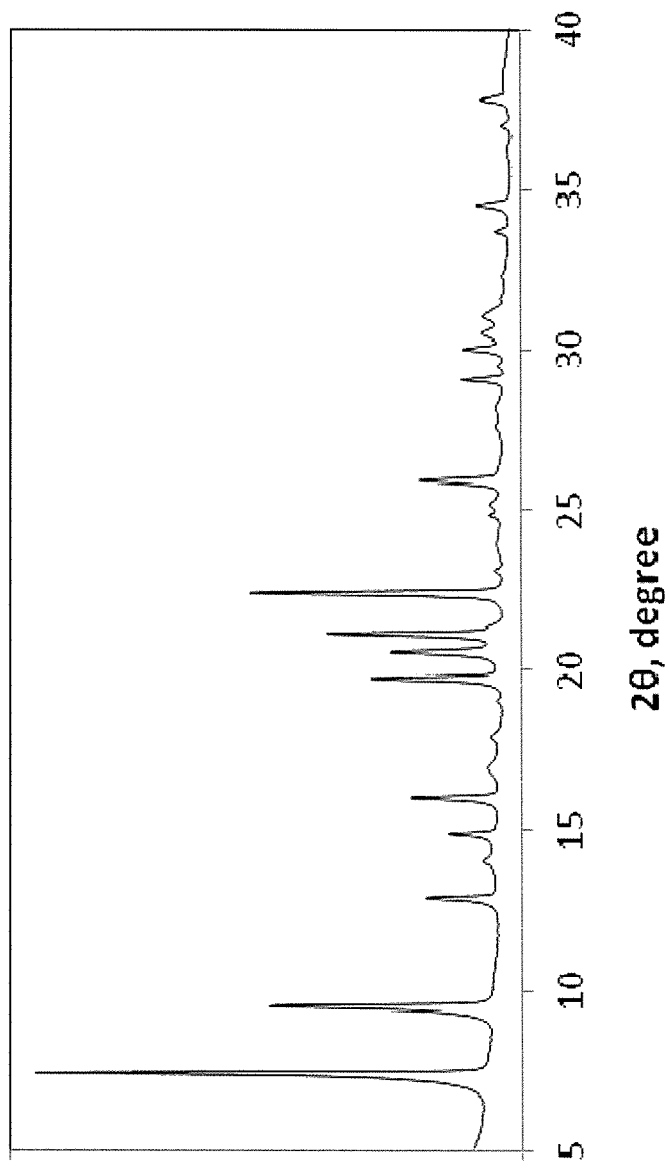

The X-ray diffraction (XRD) pattern of the solid products obtained from Comparative Example 1 is shown in FIG. 2G. The structural purity of SAPO-34 is measured to be 43%.

Comparative Example 2

A slurry was prepared in the same way of preparing the second slurry in Example 3. The slurry was then aged and crystallized under the same conditions in Example 3.

Figure 2H:
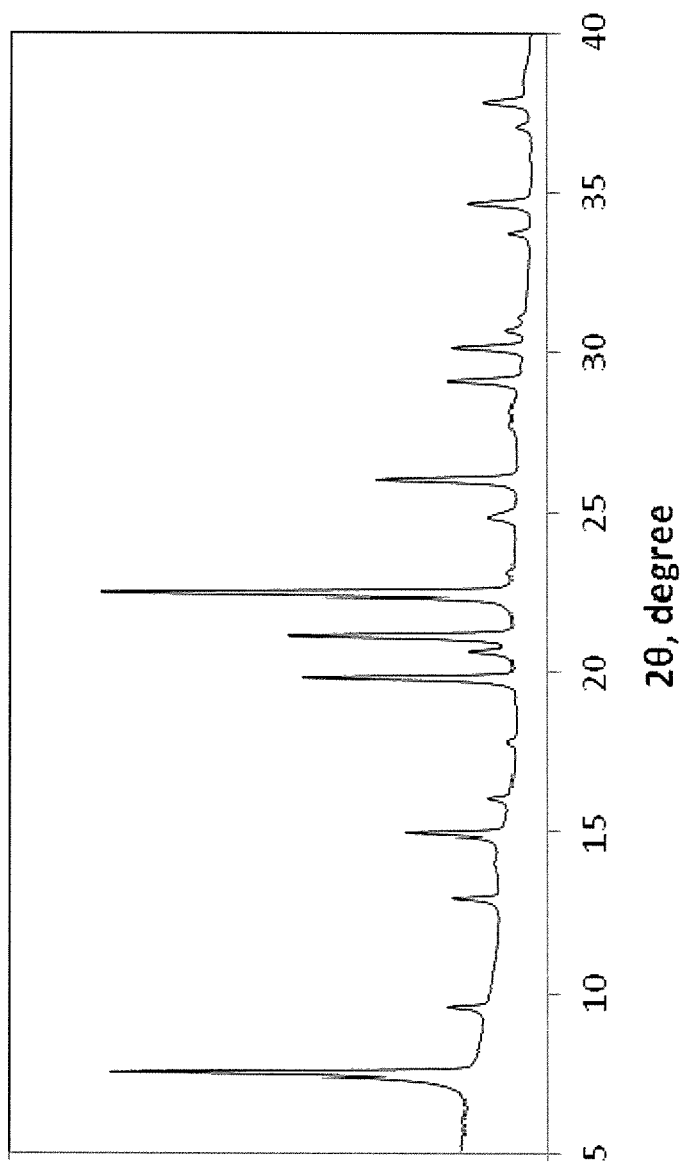
Figure 21:
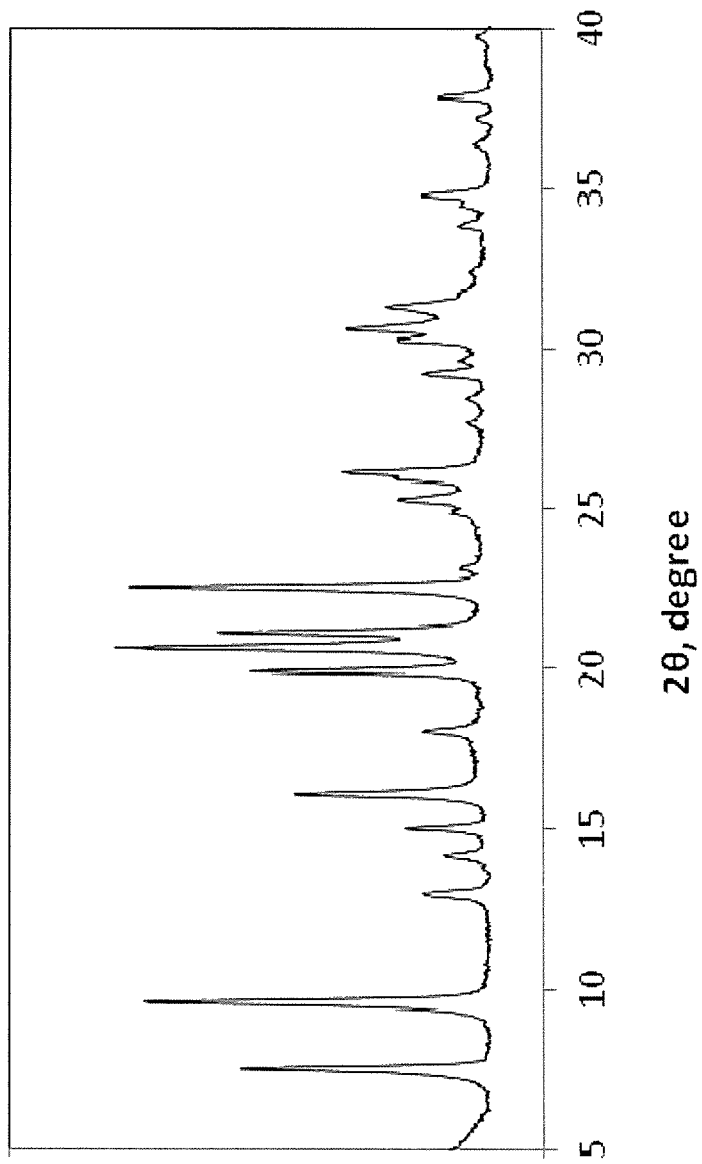

The X-ray diffraction (XRD) pattern of the solid products obtained from Comparative Example 2 is shown in FIG. 2H. The structural purity of SAPO-34 is measured to be 13%.

Comparative Example 3

96.1 g of 85% phosphoric acid ($H_3PO_4$) and 216.9 g of $H_2O$ were combined to form a diluted $H_3PO_4$ solution. Then, 55.5 g of Catapal® B alumina was added under agitation to the diluted $H_3PO_4$ solution to form a homogeneous mixture. After the addition of Catapal® B was completed, 50.4 g of Ludox® AS-30 was added into the mixture under agitation until the mixture became homogeneous. Finally, after the addition of Ludox® AS-30 was completed, the slurry was added to a premixed solution of 64.7 g of diethanolamine (DEtA) and 116.4 g of tetraethylammonium hydroxide (TEAOH) under agitation to form a slurry. The slurry was further stirred at room temperature for about 24 hours to obtain an aged slurry.

600 g of above aged slurry was transferred to a 1 L autoclave with an agitation rate of at least 200 rpm. The mixture of aged slurries was initially heated to a temperature of 120° C. and held at the temperature of 120° C. for 5 hours under autogenous pressure. Then, the mixture of aged slurries was further heated to a temperature of 190° C. and held at the temperature of 190° C. for 8 hours under autogenous pressure. The obtained solid products were filtered, washed, dried, and calcined.

The X-ray diffraction (XRD) pattern of the solid products obtained from Comparative Example 3 is shown in FIG. 2I. The structural purity of SAPO-34 is measured to be 60%.

The invention claimed is:

1. A method for synthesizing silicoaluminophosphate-34 (SAPO-34) molecular sieves, comprising:
   forming a first slurry comprising a first source of phosphorus, a first source of aluminium, a first source of silicon, and at least one first organic structure directing agent;
   aging the first slurry to form a first aged slurry;
   forming a second slurry comprising a second source of phosphorus, a second source of aluminium, a second source of silicon, and at least one second organic structure directing agent;
   aging the second slurry to form a second aged slurry;
   forming a mixture of aged slurries by combining the first aged slurry and the second aged slurry; and
   inducing crystallization of silicoaluminophosphate molecular sieves comprising the SAPO-34 molecular sieves from the mixture of aged slurries;
   wherein at least one first organic structure directing agent in the first slurry is different from at least one second organic structure directing agent in the second slurry;
   the first source of phosphorus may be the same or different from the second source of phosphorus;
   the first source of aluminium may be the same or different from the second source of aluminium; and
   the first source of silicon may be the same or different from the second source of silicon.

2. The method of claim 1, wherein forming the first slurry comprises:
   combining the first source of phosphorus and water to form a first phosphoric solution;
   introducing the first source of aluminium into the first phosphoric solution;
   introducing the first source of silicon into the first phosphoric solution after the introduction of the first source of aluminium; and
   introducing at least one first organic structure directing agent into the first phosphoric solution after the introduction of the first source of silicon.

3. The method of claim 1, wherein forming the second slurry comprises:
   combining the second source of phosphorus and water to form a second phosphoric solution;
   introducing at least one second organic structure directing agent into the second phosphoric solution;
   introducing the second source of aluminium into the second phosphoric solution after the introduction of at least one second organic structure directing agent; and
   introducing the second source of silicon into the second phosphoric solution after the introduction of the second source of aluminium.

4. The method of claim 1, wherein the first slurry is aged to produce crystal nuclei precursors, nuclei and/or crystallites for SAPO-34 in the first aged slurry.

5. The method of claim 1, wherein aging the first slurry is performed by aging the first slurry at a temperature within the range from about room temperature to about 200° C. for any period of time longer than 0.5 hours.

6. The method of claim 1, wherein aging the first slurry is performed by aging the first slurry at a temperature within the range from about 20° C. to about 150° C. for a time within the range from about 1 hour to about 30 hours.

7. The method of claim 1, wherein the second slurry is aged to produce SAPO building units with no or a very small amount of crystal nuclei precursors, nuclei, and crystallites for SAPO structures other than SAPO-34 in the second aged slurry.

8. The method of claim 1, wherein aging the second slurry is performed by aging the second slurry at a temperature within the range from about 10° C. to about 150° C. for a time within the range from about 0.5 hour to about 50 hours.

9. The method of claim 1, wherein aging the second slurry is performed by aging the second slurry at a temperature within the range from about 20° C. to about 100° C. for a time within the range from about 1 hour to about 30 hours.

10. The method of claim 1, wherein at least one first organic structure directing agent is a nitrogen compound.

11. The method of claim 1, wherein at least one second organic structure directing agent is a nitrogen compound.

12. The method of claim 1, wherein at least one first organic structure directing agent is selected from the group consisting of quaternary ammonium compounds, alkanolamines, and substituted or unsubstituted alkylamines.

13. The method of claim 1, wherein at least one first organic structure directing agent is tetraethylammonium hydroxide.

14. The method of claim 1, wherein at least one second organic structure directing agent is selected from the group consisting of quaternary ammonium compounds, alkanolamines, and substituted or unsubstituted alkylamines.

15. The method of claim 1, wherein at least one second organic structure directing agent is selected from the group consisting of alkanolamines and alkylamines.

16. The method of claim 1, wherein the weight percentage of the first aged slurry in the mixture of aged slurries is within the range from about 1% to about 99%.

17. The method of claim 1, wherein the weight percentage of the first aged slurry in the mixture of aged slurries is within the range from about 10% to about 80%.

18. The method of claim 1, wherein the weight percentage of the first aged slurry in the mixture of aged slurries is within the range from about 20% to about 50%.

19. The method of claim 1, wherein the inducing crystallization step comprises:
 initially heating the mixture of aged slurries to a first temperature within the range from about 50° C. to about 200° C. and then holding the mixture at the first temperature for a time within the range from about 0.5 hour to about 24 hours; and
 further heating the mixture of aged slurries to a second temperature within the range from about 150° C. to about 250° C. and then holding the mixture at the second temperature for a time within the range from about 0.5 hour to about 70 hours.

20. The method of claim 1, wherein the inducing crystallization step comprises:
 initially heating the mixture of aged slurries to a first temperature within the range from about 80° C. to about 150° C. and then holding the mixture at the first temperature for a time within the range from about 1 hour to about 10 hours; and
 further heating the mixture of aged slurries to a second temperature within the range from about 150° C. to about 220° C. and then holding the mixture at the second temperature for a time within the range from about 1 hour to about 50 hours.

21. The method of claim 1, wherein the inducing crystallization step comprises:
 heating the mixture of aged slurries to a temperature within the range from about 150° C. to about 250° C. and then holding the mixture at the temperature for a time within the range from about 0.5 hour to about 70 hours.

22. The method of claim 1, wherein the inducing crystallization step comprises:
 heating the mixture of aged slurries to a temperature within the range from about 150° C. to about 220° C. and then holding the mixture at the temperature for a time within the range from about 1 hour to about 50 hours.

23. The method of claim 1, wherein the silicoaluminophosphate molecular sieves comprise at least 90% of the SAPO-34 molecular sieves.

24. The method of claim 1, wherein the silicoaluminophosphate molecular sieves comprise at least 95% of the SAPO-34 molecular sieves.

25. The method of claim 1, wherein the average diameter of the SAPO-34 molecular sieves is smaller than 3 μm.

26. The method of claim 23, wherein the average diameter of the SAPO-34 molecular sieves is smaller than 3 μm.

27. A catalyst particle for the conversion of methanol to olefins comprising the SAPO-34 molecular sieves of claim 1.

28. A catalyst particle for the conversion of methanol to olefins comprising the SAPO-34 molecular sieves of claim 26.

29. A process for producing olefins, the process comprising converting methanol to olefins in the presence of the catalyst particle of claim 28.

* * * * *